United States Patent
Nomura et al.

(10) Patent No.: US 11,058,306 B2
(45) Date of Patent: Jul. 13, 2021

(54) BLOOD PRESSURE MEASURING APPARATUS

(71) Applicant: Nihon Kohden Corporation, Tokyo (JP)

(72) Inventors: Ei Nomura, Tokyo (JP); Takashi Usuda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 224 days.

(21) Appl. No.: 15/744,119

(22) PCT Filed: Jul. 7, 2016

(86) PCT No.: PCT/JP2016/003238
§ 371 (c)(1),
(2) Date: Jan. 12, 2018

(87) PCT Pub. No.: WO2017/010067
PCT Pub. Date: Jan. 19, 2017

(65) Prior Publication Data
US 2018/0220908 A1 Aug. 9, 2018

(30) Foreign Application Priority Data

Jul. 14, 2015 (JP) .............................. JP2015-140505

(51) Int. Cl.
*A61B 5/022* (2006.01)
*A61B 5/021* (2006.01)

(52) U.S. Cl.
CPC .......... *A61B 5/02141* (2013.01); *A61B 5/022* (2013.01)

(58) Field of Classification Search
CPC ........................................... A61B 5/022–0235
See application file for complete search history.

(56) References Cited

U.S. PATENT DOCUMENTS 4,501,280 A 2/1985 Hood, Jr.
6,171,254 B1 1/2001 Skelton
(Continued)

FOREIGN PATENT DOCUMENTS

CN 1513417 A 7/2004
CN 102247133 A 11/2011
(Continued)

OTHER PUBLICATIONS

Communication dated Jan. 8, 2019, issued by the Japanese Patent Office in counterpart Japanese Patent Application No. 2015-140505.
(Continued)

*Primary Examiner* — Meredith Weare
(74) *Attorney, Agent, or Firm* — Sughrue Mion, PLLC

(57) ABSTRACT

A pressurizing/depressurizing section (3) increases or decreases an internal pressure of a cuff (20). A first controlling section (4) controls an operation of the pressurizing/depressurizing section (3) so as to cause the internal pressure to transit from a pressure transient state to a pressure steady state and vice versa. A detecting section (5) detects the internal pressure. A storage section (6) stores control modes ways for increasing/decreasing the internal pressure of which are different. A determining section (7) determines a type of the cuff (20) in accordance with whether the detected internal pressure has reached the pressure steady state within a predetermined time period since start of the pressure transient state. A second controlling section (9) selects one of the control modes in accordance with the determined type of the cuff (20), and to control the operation of the pressurizing/depressurizing section (3) in accordance with the selected one of the control modes.

14 Claims, 3 Drawing Sheets

(56) References Cited

U.S. PATENT DOCUMENTS

| | | | |
|---|---|---|---|
| 2005/0261820 A1 | 11/2005 | Feeney et al. | |
| 2006/0293601 A1* | 12/2006 | Lane .................... | A61B 5/0225 600/495 |
| 2010/0298723 A1* | 11/2010 | Zhen .................. | A61B 5/02141 600/490 |
| 2011/0288423 A1 | 11/2011 | Hirahara | |
| 2011/0295130 A1* | 12/2011 | Tokko ................ | A61B 5/02141 600/494 |
| 2012/0046561 A1* | 2/2012 | Usuda ................ | A61B 5/02116 600/494 |
| 2015/0342473 A1 | 12/2015 | Hirahara | |
| 2016/0270795 A1* | 9/2016 | Krahwinkel ....... | A61B 5/02141 |
| 2018/0206745 A1* | 7/2018 | Nomura ............. | A61B 5/02141 |

FOREIGN PATENT DOCUMENTS

| | | | |
|---|---|---|---|
| CN | 102370473 A | | 3/2012 |
| JP | 59-194731 A | | 11/1984 |
| JP | 2005261820 A | | 9/2005 |

OTHER PUBLICATIONS

International Search Report dated Sep. 22, 2016, issued by the International Searching Authority in counterpart International Application No. PCT/JP2016/003238 (PCT/ISA/210).

Written Opinion dated Sep. 22, 2016, issued by the International Searching Authority in counterpart International Application No. PCT/JP2016/003238 (PCT/ISA/237).

Communication dated Jan. 6, 2020, issued by the State Intellectual Property Office of P.R. China in counterpart Chinese Application No. 201680041594.8.

* cited by examiner

BLOOD PRESSURE MEASURING APPARATUS

TECHNICAL FIELD

The present invention relates to a blood pressure measuring apparatus configured to measure blood pressure of a subject by use of a cuff.

BACKGROUND ART

In this kind of blood pressure measurement, cuffs having different volumes are used in accordance with categories of subjects including adults, children and neonates. Internal pressure of a cuff suitable for measurement of blood pressure differs from one category of subjects to another. Generally, the value of the internal pressure suitable for a child cuff is higher than the value of the internal pressure suitable for a neonate cuff, and the value of the internal pressure suitable for an adult cuff is higher than the value of the internal pressure suitable for the child cuff. Therefore, it is necessary to avoid a situation that the internal pressure of the infant cuff is set at the value suitable for the adult cuff.

In consideration of the aforementioned situation, there has been proposed an apparatus configured to automatically determine the type of a cuff connected to a blood pressure measuring apparatus. Patent Literature 1 discloses such an apparatus. Specifically, the apparatus determines the type of the cuff based on a time period between a time point at which the internal pressure of the cuff increased by air feeding reaches a first threshold and a time point at which the internal pressure then reaches a second threshold higher than the first threshold.

CITATION LIST

Patent Literature

[PTL 1] Japanese Patent Publication No. 2005-261820 A

SUMMARY OF INVENTION

Technical Problem

An object of one aspect of the invention is to improve a blood pressure measuring apparatus configured to automatically determine the type of a cuff connected to the apparatus.

Solution to Problem

According to the one aspect of the invention, there is provided a blood pressure measuring apparatus configured to measure blood pressure of a subject by use of a cuff, comprising:
  a connecting section to which a tube communicating with the cuff is connected;
  a pressurizing/depressurizing section configured to increase or decrease an internal pressure of the cuff,
  a first controlling section configured to control an operation of the pressurizing/depressurizing section so as to cause the internal pressure to transit from a pressure transient state to a pressure steady state or from the pressure steady state to the pressure transient state;
  a detecting section configured to detect the internal pressure;
  a storage section storing a plurality of control modes ways for increasing/decreasing the internal pressure of which are different;
  a determining section configured to determine a type of the cuff in accordance with whether the internal pressure detected by the detecting section has reached the pressure steady state within a predetermined time period since start of the pressure transient state; and
  a second controlling section configured to select one of the control modes in accordance with the type of the cuff determined by the determining section, and to control the operation of the pressurizing/depressurizing section in accordance with the selected one of the control modes.

With the above configuration, the cuff type is determined based on a novel viewpoint, i.e. based on whether the internal pressure of the cuff has transited to the pressure steady state within the predetermined time period after the transition to the pressure transient state. That is, the predetermined time period may be set in advance as a time period long enough for the internal pressure of the neonate cuff to transit to the pressure steady state under the control of the pressurizing/depressurizing section made by the first controlling section. Accordingly, excessive pressure higher than the value of the internal pressure of the neonate cuff which may reach the pressure steady state is not applied during determination of the type of the cuff connected to the connecting section. This fact is effective particularly in the case where a neonate whose physical tissue strength is insufficient is the subject.

DESCRIPTION OF EMBODIMENTS

Figure 1:
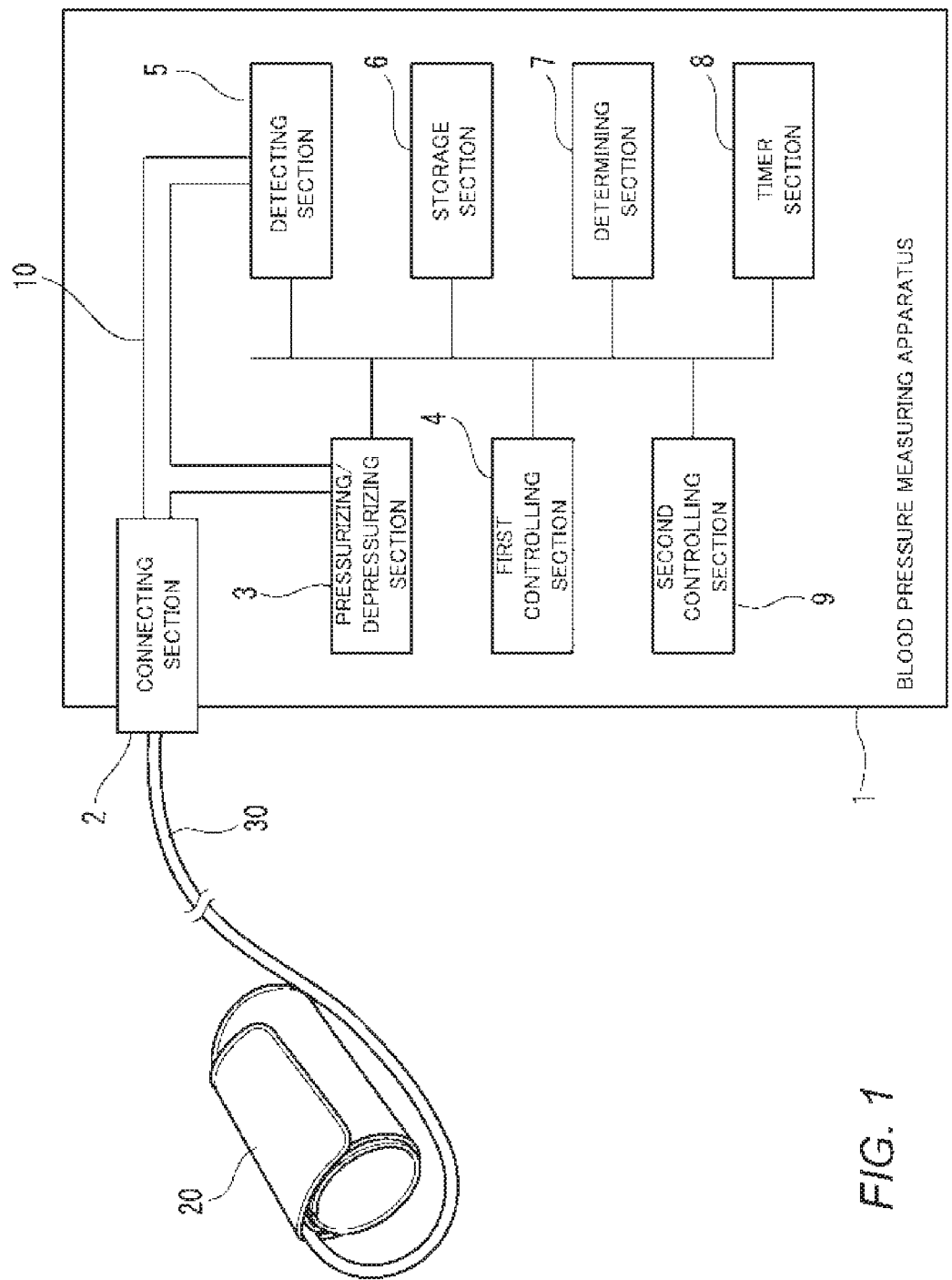
FIG. 1 is a diagram illustrating the functional configuration of a blood pressure measuring apparatus according to one embodiment.

FIG. 1 illustrates the functional configuration of a blood pressure measuring apparatus 1 according to one embodiment. The blood pressure measuring apparatus 1 is an apparatus configured to measure blood pressure of a subject by use of a cuff 20. The blood pressure measuring apparatus 1 includes a connecting section 2. A tube 30 communicating with the cuff 20 is connected to the connecting section 2.

The blood pressure measuring apparatus 1 may further include a pressurizing/depressurizing section 3, a first controlling section 4, a detecting section 5, a storage section 6, a determining section 7, a timer section 8, and a second controlling section 9.

The pressurizing/depressurizing section 3 is configured to increase or reduce internal pressure of the cuff 20. Specifically, the blood pressure measuring apparatus 1 is provided with an air way 10 communicating with the cuff 20 through the connecting section 2 and the tube 30. The pressurizing/depressurizing section 3 and the detecting section 5 are connected to the air way 10.

The pressurizing/depressurizing section 3 includes a pump function and a valve function. The pump function is to send air to the cuff 20 through the air way 10 to thereby increase the internal pressure of the cuff 20. The valve function is to establish or cancel communication between the air way 10 and ambient air. When ambient air is allowed to communicate with the air way 10 while the pump function is deactivated, the internal pressure of the cuff 20 is decreased. When ambient air is allowed to communicate with the air way 10 while the pump function is activated, the increasing speed of the internal pressure of the cuff 20 is decreased. The pump function and the valve function can be respectively implemented by an independent pump device and an independent valve device. Alternatively, the pressurizing/depressurizing section 3 may be implemented by a single device including the two functions.

The first controlling section 4 is configured to control the operation of the pressurizing/depressurizing section 3 so as to cause the internal pressure of the cuff 20 to transit from a pressure transient state to a pressure steady state or from the pressure steady state to the pressure transient state. The pressure transient state means a state in which the value of the internal pressure of the cuff 20 is changing with time. The pressure steady state means a state in which no substantial change with time can be observed in the value of the internal pressure of the cuff 20. As described above, the increase/reduction of the internal pressure of the cuff 20 can be achieved by a suitable combination of the pump function and the valve function. The first controlling section 4 is configured to adjust contribution ratios of the pump function and the valve function in the pressurizing/depressurizing section 3 to thereby cause the internal pressure of the cuff 20 to transit to the pressure transient state or the pressure steady state.

The detecting section 5 is configured to detect the internal pressure of the cuff 20. The detecting section 5 may be implemented by a pressure sensor etc.

The storage section 6 stores a plurality of control modes having different ways for increasing/reducing the internal pressure of the cuff 20. The control modes include a neonate mode and an adult mode. Specific operations of the two modes will be described later. The storage section 6 may be implemented by at least one of a memory element, a hard disk and a portable recording medium.

The determining section 7 is configured to determine the type of the cuff 20 in accordance with whether the internal pressure of the cuff 20 detected by the detecting section 5 has reached the pressure steady state within a predetermined time period since start of the pressure transient state. The predetermined time period is counted by the timer section 8. The operation will be described later in detail.

The second controlling section 9 is configured to select one from the control modes stored in the storage section 6 based on the type of the cuff 20 determined by the determining section 7 to thereby control the operation of the pressurizing/depressurizing section 3 based on the selected control mode. The operation will be described later in detail.

Figure 2:
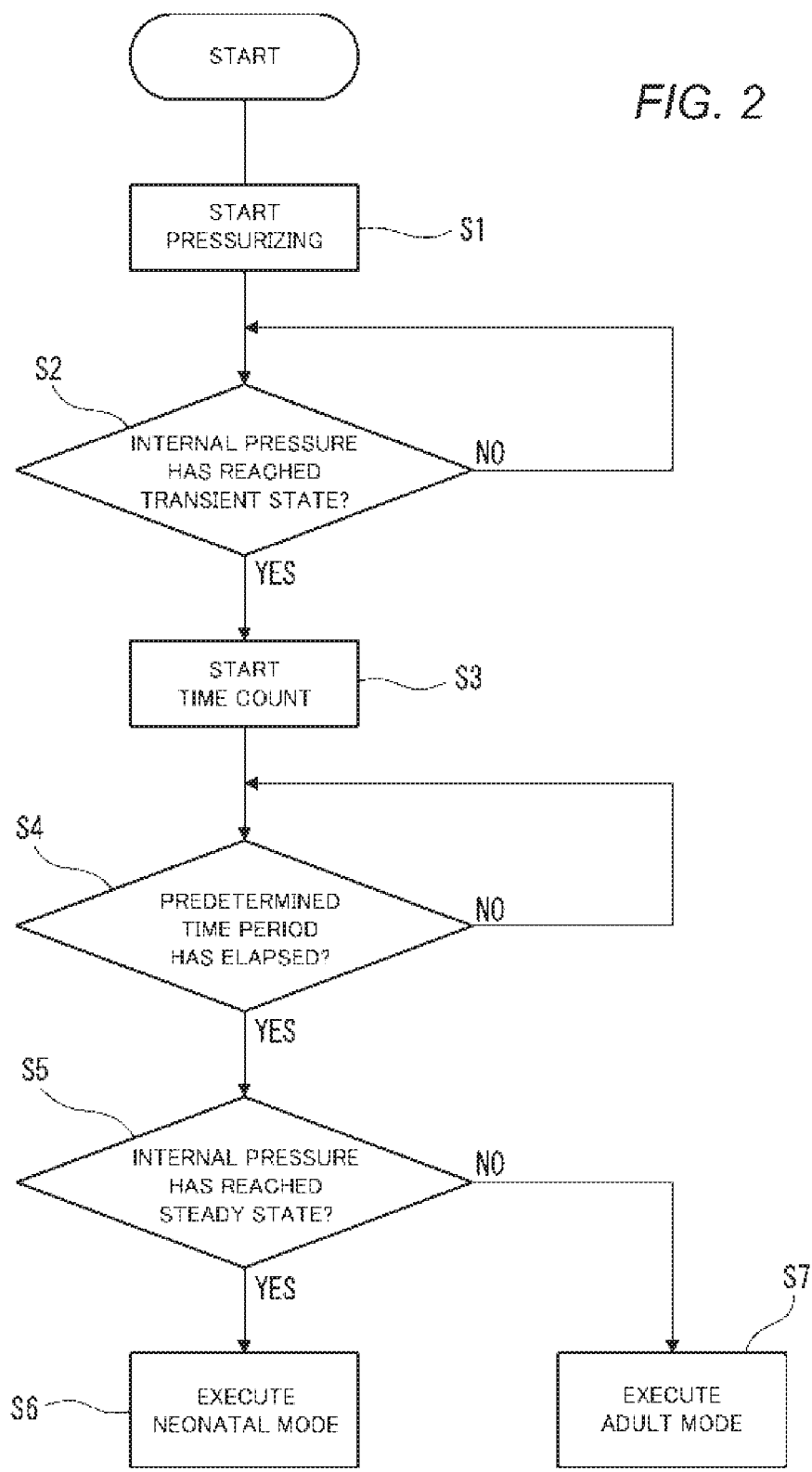
FIG. 2 is a flowchart illustrating control performed by the blood pressure measuring apparatus.
Figure 3:
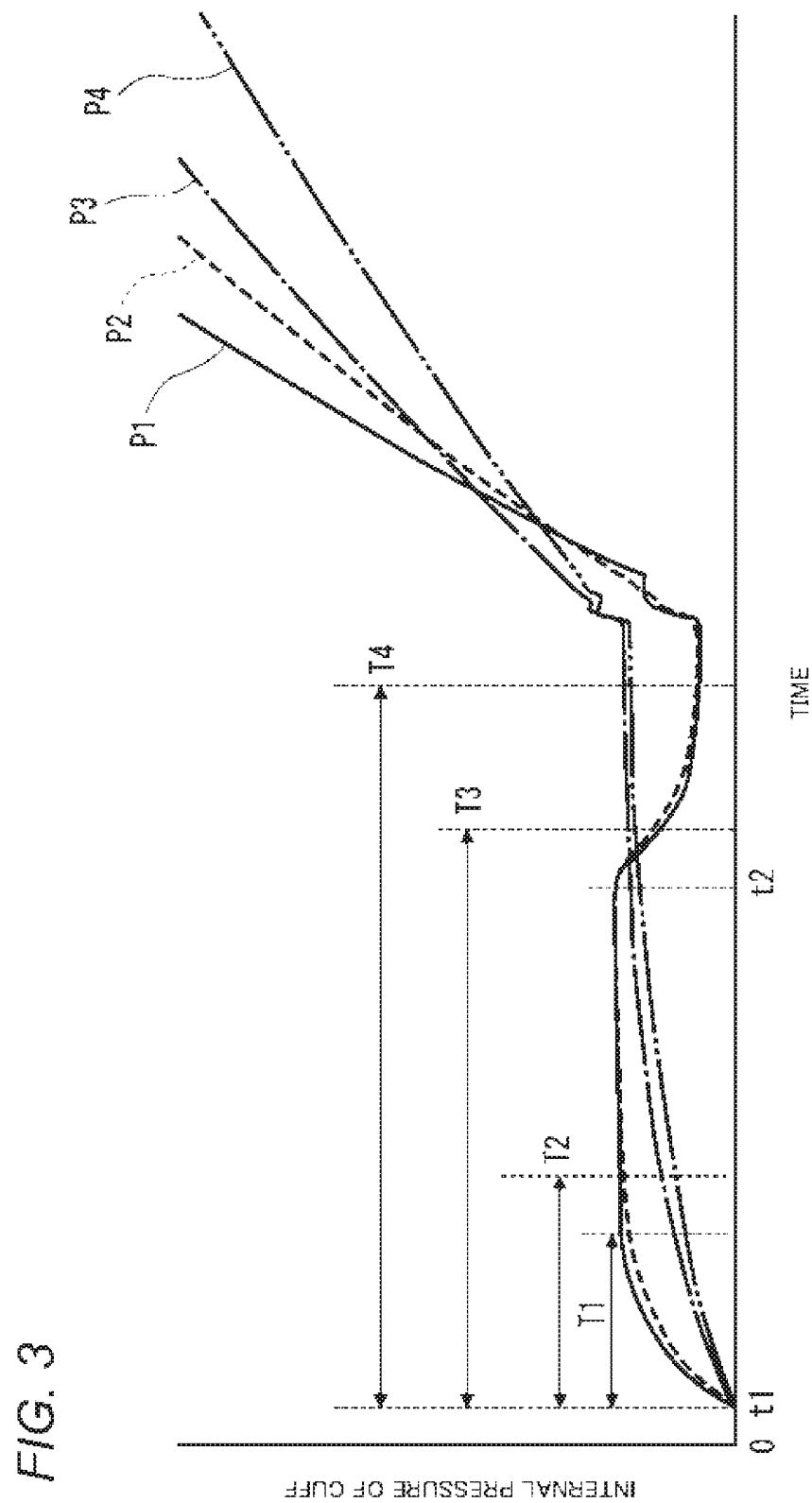
FIG. 3 is a diagram for explaining the control performed by the blood pressure measuring apparatus.

Next, specific operation of the blood pressure measuring apparatus 1 will be described with reference to FIGS. 2 and 3. FIG. 2 is a flowchart illustrating the operation executed by the blood pressure measuring apparatus 1. FIG. 3 illustrates change of the internal pressure of the cuff 20 with time. The change is achieved by the blood pressure measuring apparatus 1. A solid line designates an internal pressure change characteristic P1 in a case where the cuff 20 is used as a relatively small neonate cuff. A dashed line designates an internal pressure change characteristic P2 in a case where the cuff 20 is used as a relatively large neonate cuff. A chain line designates an internal pressure change characteristic P3 in a case where the cuff 20 is used as a relatively small adult cuff. A dashed chain line designates an internal pressure change characteristic P4 in a case where the cuff 20 is used as a relatively large adult cuff.

First, the pressurizing/depressurizing section 3 is driven by the first controlling section 4 to thereby start to pressurize the cuff 20 (step S1). The determining section 7 determines whether the internal pressure of the cuff 20 has transited to the pressure transient state or not, based on the internal pressure of the cuff 20 detected by the detecting section 5 (step S2). When the internal pressure of the cuff 20 starts to increase as shown in FIG. 3, it is determined that the internal pressure of the cuff 20 has transited to the pressure transient state (YES in the step S2). The determining section 7 repeats the aforementioned determination process (NO in the step S2) until the shift to the pressure transient state is detected.

When the transition to the pressure transient state is determined, the timer section 8 starts to count time (step S3). A time point t1 in FIG. 3 indicates a starting time point of the time count.

The determining section 7 determines whether a predetermined time period has elapsed or not since the starting time point t1 of the pressure transient state (that is, the starting time point of the time count) (step S4). In the example, a time period from the time point t1 to a time point t2 in FIG. 3 corresponds to the aforementioned predetermined time period. The determining section 7 repeats the aforementioned determination process (NO in the step S4) until a lapse of the predetermined time period is detected.

When the lapse of the predetermined time is detected (YES in the step S4), the determining section 7 determines whether the internal pressure of the cuff 20 has transited to the pressure steady state or not, based on the internal pressure of the cuff 20 detected by the detecting section 5 (step S5).

When it is determined that the internal pressure of the cuff 20 has transited to the pressure steady state at the time point t2 at which the predetermined time period has elapsed (YES in the step S5), the determining section 7 determines that the cuff 20 connected to the connecting section 2 is a neonate cuff. In this case, the second controlling section 9 controls the operation of the pressurizing/depressurizing section 3 based on the neonate mode stored in the storage section 6 (step S6).

For example, in each of the internal pressure change characteristics P1 and P2 in FIG. 3, the internal pressure of the cuff 20 is regarded as having transited to the pressure steady state due to no substantial change in the value of the internal pressure at the time point t2. Therefore, the determining section 7 determines that the cuff 20 showing the internal pressure change characteristic is a neonate cuff.

The neonatal mode executed by the second controlling section 9 includes a first period and a second period. In the first period, the internal pressure of the cuff 20 is once reduced to be lower than the value at the time point t2. In the second period following the first period, the internal pressure of the cuff 20 is increased to be higher than the value at the time point t2. Blood pressure of the subject is measured in the second period. The second controlling section 9 suitably combines the pump function and the valve function of the pressurizing/depressurizing section 3 to thereby carry out the operation. For example, air feeding capability achieved by the pump function of the pressurizing/depressurizing section 3 is made relatively low in the first period. Thus, the internal pressure of the cuff 20 decreases. Air discharging capability of the pressurizing/depressurizing section 3 is reduced or invalidated in the second period. Thus, the increase of the internal pressure for measurement of the blood pressure can be attained.

When it is determined that the internal pressure of the cuff 20 has not transited to the pressure steady state yet at the time point t2 at which the predetermined time period has elapsed (NO in the step S5), the determining section 7 determines that the cuff 20 connected to the connecting section 2 is an adult cuff. In this case, the second controlling section 9 controls the operation of the pressurizing/depressurizing section 3 based on the adult mode stored in the storage section 6 (step S7).

For example, in each of the internal pressure change characteristics P3 and P4 in FIG. 3, the internal pressure of the cuff 20 is regarded as still being in the pressure transient state due to the increase in the value of the internal pressure at the time point t2. Therefore, the determining section 7 determines that the cuff 20 exhibiting such a internal pressure change characteristic is an adult cuff.

The adult mode executed by the second controlling section 9 includes a first period and a second period. In the first period, the internal pressure of the cuff 20 is continuously increased with a relatively low pressure gradient. In the second period following the first period, the internal pressure of the cuff 20 is increased with a relatively high pressure gradient. Blood pressure of the subject is measured in the second period. The second controlling section 9 suitably combines the pump function and the valve function of the pressurizing/depressurizing section 3 to carry out the operation. For example, air discharging capability configured to be achieved by the valve function of the pressurizing/depressurizing section 3 is reduced or invalidated in the second period. Thus, the increase of the internal pressure for measurement of the blood pressure can be attained.

As described above, in the blood pressure measuring apparatus 1 according to the embodiment, the cuff type is determined based on a novel viewpoint, i.e. based on whether the internal pressure of the cuff 20 has transited to the pressure steady state within the predetermined time period after the transition to the pressure transient state. That is, the predetermined time period may be set in advance as a time period long enough for the internal pressure of the neonate cuff to transit to the pressure steady state under the control of the pressurizing/depressurizing section 3 made by the first controlling section 4. One second may be used as an example of the predetermined time period. Excessive pressure higher than the value of the internal pressure of the neonate cuff which may reach the pressure steady state is not applied during determination of the type of the cuff 20 connected to the connecting section 2. This fact is effective particularly in the case where a neonate whose physical tissue strength is insufficient is the subject.

When it is determined by the determining section 7 that the cuff 20 is a neonate cuff, the internal pressure of the cuff 20 is reduced once by the second controlling section 9. Thus, it is possible to suppress accumulation of oppression pressure applied by the cuff 20 onto a neonate whose physical tissue strength is insufficient. In addition, since pressurizing for measurement of blood pressure starts at the state in which the internal pressure has been reduced once, measurement based on pressurizing can be carried out effectively on the neonate whose blood pressure distribution is relatively low.

In the blood pressure measuring apparatus 1 according to the embodiment, the timer section 8 may be configured to measure a time period since the start of the pressure transient state (time point t1) until the internal pressure of the cuff 20 detected by the detecting section 5 reaches the pressure steady state. In the case of the internal pressure change characteristic P1 shown in FIG. 3, a time period T1 corresponds to the above time period. Same or similarly, in the case of the internal pressure change characteristic P2, a time period T2 corresponds to the above time period. In the case of the internal pressure change characteristic P3, a time period T3 corresponds to the above time period. In the case of the internal pressure change characteristic P4, a time period T4 corresponds to the above time period.

The time period until the internal pressure reaches the pressure steady state (time constant) differs from one cuff to another when there is a difference in volume between the cuffs even though the cuffs belong to the same subject category (neonate, adults etc.). Specifically, the relation between the volume V and the time period (time constant) [tau] required until the internal pressure reaches the pressure steady state can be expressed by the following expression.

$$P = P1[1 - \exp(-t/[tau])]$$

$$[tau] = V \cdot R$$

Here, P designates the internal pressure of the cuff 20, P1 designates the internal pressure of the cuff 20 in the pressure steady state and R designates resistance of a flow path including the air way 10 and the tube 30.

Accordingly, the determining section 7 is configured to determine the type of the cuff 20 based on the time (time constant) [tau] counted by the timer section 8. For example, cuffs may be classified into a cuff having a relatively small volume and a cuff having a relatively large volume, based on the lengths of the times T1 and T2, even though the cuffs belong to the same category of neonate. Similarly, cuffs may be classified into a cuff having a relatively small volume and a cuff having a relatively large volume, based on the lengths of the times T3 and T4, even though the cuffs belong to the same category of adults.

In the example, four control modes having different methods for increasing/reducing the internal pressure in accordance with the four cuff types classified thus are stored in the storage section 6. The second controlling section 9 is configured to select one from the four control modes in accordance with the cuff type determined by the determining section 7 and control the operation of the pressurizing/depressurizing section 3 based on the selected control mode.

In this case, more detailed classification of cuff types can be made particularly in the viewpoint of the volume. The operation of the pressurizing/depressurizing section 3 during measurement of blood pressure based on the more detailed classification can be performed suitably.

In the blood pressure measuring apparatus 1 according to the embodiment, the second controlling section 9 may be configured to select one from the control modes stored in the storage section 6 and not to stop the operation of the pressurizing/depressurizing section 3 when operation control of the pressurizing/depressurizing section 3 is started based on the selected control mode.

In the example shown in FIG. 3, when the neonate mode is selected at the time point t2, the second controlling section 9 does not stop but relatively reduces the air feeding function of the pressurizing/depressurizing section 3. In this manner, the second controlling section 9 reduces the internal pressure of the cuff 20 and proceeds to the following pressurizing process for measurement of blood pressure. In addition, when the adult mode is selected at the time point t2, the second controlling section 9 does not stop but maintains the air feeding function of the pressurizing/depressurizing section 3. In this manner, the second controlling section 9 proceeds to the following pressurizing process for measurement of blood pressure.

According to such a configuration, the operation of the pressurizing/depressurizing section 3 does not have to be stopped during determination of the type of the cuff 20, but seamless shift to the pressurizing process for measurement of blood pressure can be performed. Accordingly, measurement of blood pressure can be performed more rapidly.

In the blood pressure measuring apparatus 1 according to the embodiment, the first controlling section 4 may be configured to cause the pressurizing/depressurizing section 3 to communicate with ambient air at least while the internal pressure of the cuff 20 is in the pressure transient state. Specifically, air feeding achieved by the pump function of the pressurizing/depressurizing section 3 is performed while the air discharging function achieved by the valve function of the pressurizing/depressurizing section 3 is at least partially validated.

According to such a configuration, the internal pressure of the cuff 20 transiting to the pressure steady state can be kept relatively low. Accordingly, in the case where a neonate whose biological tissue strength is insufficient is the subject, the load of pressurizing made by the cuff 20 can be suppressed. In addition, since the transition to the pressure steady state can be achieved relatively early, determination of the cuff type and transition to the following pressurizing process for measurement of blood pressure can be performed rapidly.

In the blood pressure measuring apparatus 1 according to the embodiment, the internal pressure of the cuff 20 in the pressure steady state (that is, the internal pressure for distinguishing the neonate cuff) may be set to be less than 30 mm Hg. Preferably, the internal pressure may be set to be less than 15 mmHg. More preferably, the internal pressure may be set to be less than 5 mmHg.

Assume that the value of the internal pressure about determination of the cuff type is less than 30 mmHg. In this case, even when the adult mode is selected so as not to reduce the internal pressure of the cuff 20 once, measurement based on pressurizing can be carried out effectively on a subject whose blood pressure distribution is relatively low.

Assume that the value of the internal pressure about determination of the cuff type is less than 15 mmHg. In this case, the internal pressure is not regarded as a "pressurizing state" on an adult subject in connection with the IEC 80601-2-30:2009 standard. Thus, the apparatus is free from various constraints as to the duration etc. of the "pressurizing state" so that the degree of freedom in designing the apparatus can be further improved.

Assume that the value of the internal pressure about determination of the cuff type is less than 5 mmHg. In this case, the internal pressure is not regarded as a "pressurizing state" on a neonate subject in connection with the IEC 80601-2-30:2009 standard. Thus, the apparatus is free from various constraints as to the duration etc. of the "pressurizing state" so that the degree of freedom in designing the apparatus can be further improved.

The aforementioned embodiments are merely exemplified in order to make the invention easy to understand. The configuration according to each of the aforementioned embodiments can be appropriately changed or modified without departing from the concept of the invention. In addition, it is obvious that equivalents are contained in the scope of the invention.

In the aforementioned embodiments, either the neonatal mode or the adult mode can be executed. However, configuration may be made so that a child cuff having an intermediate volume between the neonate cuff and the adult cuff can be distinguished. In this case, in addition to the aforementioned predetermined time period (time period from the time point t1 to the time point t2) for making determination for distinguishing the neonate cuff, another predetermined time period (time period from the time point t1 to a time point after the time point t2) which is a time period long enough for the internal pressure of the child cuff to transit to the pressure steady state under the control of the pressurizing/depressurizing section 3 made by the first controlling section 4 may be set in advance.

In the aforementioned embodiments, the functions of the first controlling section 4, the determining section 7, the timer section 8, and the second controlling section 9 are at least partially implemented by software executed by the cooperation of a processor and a memory which are connected to each other communicatively. A CPU or an MPU may be used as an example of the processor. An RAM or an ROM may be used as an example of the memory. However, at least one of the functions of the first controlling section 4, the determining section 7, the timer section 8, and the second controlling section 9 may be implemented by hardware such as a circuit element or by a combination of hardware and software. In addition, at least two of the first controlling section 4, the determining section 7, the timer section 8 and the second controlling section 9 may be implemented by a common processor and a common memory.

The present application is based on Japanese Patent Application No. 2015-140505 filed on Jul. 14, 2015, the contents of which are hereby incorporated by reference.

The invention claimed is:

1. A blood pressure measuring apparatus configured to measure blood pressure of a subject by use of a cuff, comprising:
   a connector to which a tube communicating with the cuff is connected;
   a pressurizing/depressurizing section comprising a pump and a valve configured to increase and decrease an internal pressure of the cuff;
   a detector configured to detect the internal pressure of the cuff;
   a memory storing a plurality of blood pressure measurement modes for increasing/decreasing the internal pressure of the cuff; and
   a processor configured to:
      control the pressurizing/depressurizing section to increase the internal pressure of the cuff from a first pressure steady state in which the internal pressure of the cuff is a first internal pressure to a second pressure steady state in which the internal pressure of the cuff is a second internal pressure greater than the first internal pressure,
      determine a time over which the pressurizing/depressurizing section increases the internal pressure of the cuff from the first pressure steady state to the second pressure steady state,
      determine a type of the cuff based on the time over which the pressurizing/depressurizing section increases the internal pressure of the cuff from the first pressure steady state to the second pressure steady state,
      select a blood pressure measurement mode among the plurality of blood pressure measurement modes in accordance with the type of the cuff,
      control the pressurizing/depressurizing section to control the internal pressure of the cuff in accordance with the selected blood pressure measurement mode, and measure the blood pressure of the subject using the selected blood pressure measurement mode.

2. The blood pressure measuring apparatus according to claim 1, further comprising:
a timer configured to measure the time over which the pressurizing/depressurizing section increases the internal pressure of the cuff from the first pressure steady state to the second pressure steady state,
wherein the processor is configured to determine the type of the cuff in accordance with the time measured by the timer.

3. The blood pressure measuring apparatus according to claim 1, wherein the processor is configured to select the selected blood pressure measurement mode without stopping the operation of the pressurizing/depressurizing section, and if the selected blood pressure measurement mode is a neonate blood pressure measurement mode to start to measure the blood pressure of the subject in a state in which the internal pressure of the cuff is less than the second internal pressure, in accordance with the neonate blood pressure measurement mode and if the selected blood pressure measurement mode is an adult blood pressure measurement mode to start to measure the blood pressure of the subject in a state in which the internal pressure of the cuff is greater than the second internal pressure.

4. The blood pressure measuring apparatus according to claim 1, wherein the processor is configured to cause the pressurizing/depressurizing section to open the valve to receive ambient air and operate the pump to increase the internal pressure of the cuff from the first pressure steady state to the second pressure steady state.

5. The blood pressure measuring apparatus according to claim 1, wherein the second internal pressure of the cuff in the second pressure steady state is less than 30 mmHg.

6. The blood pressure measuring apparatus according to claim 1, wherein the processor is configured to cause the pressurizing/depressurizing section to control the internal pressure of the cuff by closing the valve to ambient air and operating the pump to increase the internal pressure of the cuff and by opening the valve to ambient air and operating the pump to decrease the internal pressure of the cuff.

7. The blood pressure measuring apparatus according to claim 1, wherein the selection of the blood pressure measurement mode is performed prior to a pressurizing process for measurement of the blood pressure of the subject in the blood pressure measurement mode.

8. A method of controlling a blood pressure measuring apparatus configured to measure blood pressure of a subject by use of a cuff, the blood pressure measuring apparatus comprising a connector to which a tube communicating with the cuff is connected, a pressurizing/depressurizing section comprising a pump and a valve configured to increase and decrease an internal pressure of the cuff, a memory storing a plurality of blood pressure measurement modes for increasing/decreasing the internal pressure of the cuff, and a processor, wherein the method of controlling the blood pressure measuring apparatus to measure the blood pressure of the subject comprises:
detecting the internal pressure of the cuff;
controlling by the processor the pressurizing/depressurizing section to increase the internal pressure of the cuff from a first pressure steady state in which the internal pressure of the cuff is a first internal pressure to a second pressure steady state in which the internal pressure of the cuff is a second internal pressure greater than the first internal pressure;
determining by the processor a time over which the pressurizing/depressurizing section increases the internal pressure of the cuff from the first pressure steady state to the second pressure steady state;
determining by the processor a type of the cuff based on the time over which the pressurizing/depressurizing section increases the internal pressure of the cuff from the first pressure steady state to the second pressure steady state;
selecting by the processor a blood pressure measurement mode among the plurality of blood pressure measurement modes in accordance with the type of the cuff;
controlling by the processor the pressurizing/depressurizing section to control the internal pressure of the cuff in accordance with the selected blood pressure measurement mode; and
measuring by the processor the blood pressure of the subject using the selected blood pressure measurement mode.

9. The method according to claim 8, further comprising:
measuring the time over which the pressurizing/depressurizing section increases the internal pressure of the cuff from the first pressure steady state to the second pressure steady state by a timer,
wherein the determining the type of the cuff comprises determining the type of the cuff in accordance with the time measured by the timer.

10. The method according to claim 8, wherein the selecting the blood pressure measurement mode comprises selecting the blood pressure measurement mode without stopping the operation of the pressurizing/depressurizing section, and if the selected blood pressure measurement mode is a neonate blood pressure measurement mode starting to measure the blood pressure of the subject in a state in which the internal pressure of the cuff is less than the second internal pressure, in accordance with the neonate blood pressure measurement mode, and if the selected blood pressure measurement mode is an adult blood pressure measurement mode starting to measure the blood pressure of the subject in a state in which the internal pressure of the cuff is greater than the second internal pressure.

11. The method according to claim 8, wherein the pressurizing/depressurizing section opens the valve to receive ambient air and operates the pump to increase the internal pressure of the cuff from the first pressure steady state to the second pressure steady state.

12. The method according to claim 8, wherein the second internal pressure of the cuff in the second pressure steady state is less than 30 mmHg.

13. The method according to claim 8, wherein the pressurizing/depressurizing section controls the internal pressure of the cuff by closing the valve to ambient air and operating the pump to increase the internal pressure of the cuff and by opening the valve to ambient air and operating the pump to decrease the internal pressure of the cuff.

14. The method according to claim 8, wherein the selecting the blood pressure measurement mode comprises selecting the blood pressure measurement mode prior to a pressurizing process for measurement of the blood pressure of the subject in the blood pressure measurement mode.

* * * * *